United States Patent
Chen et al.

(10) Patent No.: US 11,510,949 B2
(45) Date of Patent: Nov. 29, 2022

(54) **USE OF THE TREATMENT OR IMPROVEMENT OF SLEEP DISORDERS BY *LACTOBACILLUS BREVIS* PROGA28 AND/OR ITS METABOLITES**

(71) Applicant: SYNGEN BIOTECH CO., LTD, Tainan (TW)

(72) Inventors: Wei-Jen Chen, Tainan (TW); Bing-Huang Gau, Tainan (TW); Po-An Chen, Tainan (TW); Yu-Shan Wei, Tainan (TW)

(73) Assignee: SYNGEN BIOTECH CO., LTD, Tainan (TW)

(*) Notice: Subject to any disclaimer, the term of this patent is extended or adjusted under 35 U.S.C. 154(b) by 145 days.

(21) Appl. No.: 16/937,248

(22) Filed: Jul. 23, 2020

(65) Prior Publication Data
US 2021/0023148 A1  Jan. 28, 2021

(30) Foreign Application Priority Data
Jul. 25, 2019 (TW) .................................. 108126440

(51) Int. Cl.
*A61K 35/747* (2015.01)
*C12N 5/00* (2006.01)

(52) U.S. Cl.
CPC .......... *A61K 35/747* (2013.01); *C12N 5/0018* (2013.01); *C12N 2500/32* (2013.01)

(58) Field of Classification Search
CPC ......................... A61K 35/747; C12R 2001/24
See application file for complete search history.

(56) References Cited

FOREIGN PATENT DOCUMENTS

| EP | 2821073 A1 | 1/2015 |
|---|---|---|
| KR | 101968242 B1 | 4/2019 |

OTHER PUBLICATIONS

Fukao et al., "Genomic Analysis by Deep Sequencing of the Priobiotic Lactobacillus brevis KB290 Harboring Nine Plasmids Reveals Genomic Stability", PLOS ONE, 8(3), pp. 1-10 (Year: 2013).*

Higo-Yamamoto et al., "Dietary Heat-Killed *Lactobacillus brevis* SBC8803 Attenuates Chronic Sleep Disorders Induced by Psychophysiological Stress in Mice," J. Nutr Sci Vitaminol, vol. 65, pp. 164-170, 2019.

* cited by examiner

*Primary Examiner* — Michelle F. Paguio Frising
*Assistant Examiner* — Grant C Currens
(74) *Attorney, Agent, or Firm* — Muncy, Geissler, Olds & Lowe, P.C.

(57) ABSTRACT

The present invention relates to the use of a novel *Lactobacillus brevis* ProGA28 strain, deposited in the German Collection for Microorganisms and Cell Cultures (DSMZ) under the accession number DSM 33167 on May 28, 2019. The metabolites of *Lactobacillus brevis* ProGA28 have the ability to improve sleep quality, can effectively reduce the time of rapid eye movement in the sleep phase, can reduce time to fall asleep, can increase total sleep time, and can increase the ratio of low waves during sleep so that sleep disorders and related complications, such as anxiety and immune system diseases, are treated.

6 Claims, 18 Drawing Sheets

Specification includes a Sequence Listing.

SEQUENCE LISTING

<160> NUMBER OF SEQ ID NOS: 1

<210> SEQ ID NO 1
<211> LENGTH: 1518
<212> TYPE: DNA
<213> ORGANISM: Lactobacillus brevis

<400> SEQUENCE: 1

```
gacgaacgct ggcggcatgc ctaatacatg caagtcgaac gagcttccgt tgaatgacgt      60
gcttgcactg atttcaacaa tgaagcgagt ggcgaactgg tgagtaacac gtgggaaatc     120
tgcccagaag caggggataa cacttggaaa caggtgctaa taccgtataa caacaaaatc     180
cgcatggatt ttgtttgaaa ggtggcttcg gctatcactt ctggatgatc ccgcggcgta     240
```

```
ttagttagtt ggtgaggtaa aggcccacca agacgatgat acgtagccga cctgagaggg    300
taatcggcca cattgggact gagacacggc ccaaactcct acgggaggca gcagtaggga    360
atcttccaca atggacgaaa gtctgatgga gcaatgccgc gtgagtgaag aagggtttcg    420
gctcgtaaaa ctctgttgtt aaagaagaac acctttgaga gtaactgttc aagggttgac    480
ggtatttaac cagaaagcca cggctaacta cgtgccagca gccgcggtaa tacgtaggtg    540
gcaagcgttg tccggattta ttgggcgtaa agcgagcgca ggcggttttt taagtctgat    600
gtgaaagcct tcggcttaac cggagaagtg catcggaaac tgggagactt gagtgcagaa    660
gaggacagtg gaactccatg tgtagcggtg gaatgcgtag atatatggaa gaacaccagt    720
ggcgaaggcg gctgtctagt ctgtaactga cgctgaggct cgaaagcatg ggtagcgaac    780
aggattagat accctggtag tccatgccgt aaacgatgag tgctaagtgt tggagggttt    840
ccgcccttca gtgctgcagc taacgcatta agcactccgc ctggggagta cgaccgcaag    900
gttgaaactc aaaggaattg acggggaccc gcacaagcgg tggagcatgt ggtttaattc    960
gaagctacgc gaagaacctt accaggtctt gacatcttct gccaatctta gagataagac   1020
gttcccttcg gggacagaat gacaggtggt gcatggttgt cgtcagctcg tgtcgtgaga   1080
tgttgggtta agtcccgcaa cgagcgcaac ccttattatc agttgccagc attcagttgg   1140
gcactctggt gagactgccg gtgacaaacc ggaggaaggt ggggatgacg tcaaatcatc   1200
atgcccctta tgacctgggc tacacacgtg ctacaatgga cggtacaacg agtcgcgaag   1260
tcgtgaggct aagctaatct cttaaagccg ttctcagttc ggattgtagg ctgcaactcg   1320
cctacatgaa gttggaatcg ctagtaatcg cggatcagca tgccgcggtg aatacgttcc   1380
cgggccttgt acacaccgcc cgtcacacca tgagagtttg taacacccaa agccggtgag   1440
ataaccttcg ggagtcagcc gtctaaggtg ggacagatga ttagggtgaa gtcgtaacaa   1500
ggtagccgta ggagaacc                                                 1518
```

USE OF THE TREATMENT OR IMPROVEMENT OF SLEEP DISORDERS BY *LACTOBACILLUS BREVIS* PROGA28 AND/OR ITS METABOLITES

BACKGROUND OF THE INVENTION

Field of the Invention

This invention relates to a probiotic and its use. More particularly, the present invention relates to a use of the treatment or improvement of sleep disorders by *Lactobacillus brevis* ProGA28 and/or its metabolites.

Description of the Related Art

According to research, the average sleep time of the adults is about 7-8 hours. The sleep disorders mean that someone has problems with quality, timing, and amount of sleep, for example, the sleep time is too short, it is difficult to fall asleep, or the sleep will be interrupted for no reason.

The sleep disorders not only cause symptoms such as poor spirits, inattention, and immune system damage, but also have some adverse effects on health, such as increasing blood pressure and increasing the risk of having an acute heart attack, cancers, digestive system disorders, mental illness, etc. However, there are many reasons of sleep disorders, such as excessive stress, anxiety, sleep apnea, changes in work and rest habits. Therefore, it is not a simple matter to treat sleep disorders clinically.

The previous studies suggested that oral administration of γ-aminobutyric acid (GABA) can inhibit the neurotransmitter of the central nervous system, so that the brain can be relax and to stabilize, and then to improve sleep. However, the current animal experiments confirmed that taking pure GABA has a limited effect on improving sleep quality, in other words, taking a composition including GABA is not helpful to improve the sleep disorders.

SUMMARY OF THE INVENTION

The main propose of this present invention is to provide a use of *Lactobacillus brevis* ProGA28 and its metabolites thereof, in particularly, the *Lactobacillus brevis* ProGA28's metabolites has the ability to improve sleep quality and can effectively reduce the phase time of the rapid eye movement sleep, reduce the number of falling asleep, and increase the overall sleep time and prolong the single falling asleep time, and also can increase the slow-wave ratio of brain waves in sleep, so as to treat or improve sleep disorders and related complications, such as anxiety The effect of disease, immune system disease.

In order to achieve the above purposes, the present invention discloses an isolated strain of *Lactobacillus brevis* ProGA28 deposited at the Leibniz Institute DSMZ-German Collection of Microorganisms and Cell Cultures (DSM) on 28$^{th}$ May, 2018 under accession number DSM 33167, and deposited at Taiwan Bioresource Collection and Research Center (BCRC) of Food Industry Research and Development Institute on 27$^{th}$ Jun., 2019 under accession number BCRC 910910.

The 16S rRNA sequence of *Lactobacillus brevis* ProGA28 is shown as SEQ ID NO: 1.

The *Lactobacillus brevis* ProGA28 is isolated from a fermented pickle.

In one embodiment of this invention, after the *Lactobacillus brevis* ProGA28 is cultured in a medium containing monosodium glutamate, the bacteria of *Lactobacillus brevis* ProGA28 are removed and then obtain the metabolites of the *Lactobacillus brevis* ProGA28, which are used for treating or to improving the sleep disorders.

In other words, by administering an effective amount of *Lactobacillus brevis* ProGA28, its metabolites, or a composition containing any of the above substances to a patient suffering from sleep disorders or poor sleep quality, it can effectively improve the patient's sleep quality and increase the patient's sleep time to achieve the effect of curing or improving the sleep disorders.

In another embodiment of this invention, it disclosed the use of *Lactobacillus brevis* ProGA28 or its metabolites for preventing the sleep disorders. Because the *Lactobacillus brevis* ProGA28 or its metabolites disclosed in the present invention have the ability to improve sleep quality and stabilize brain waves, by administering an effective amount of *Lactobacillus brevis* ProGA28, its metabolites, or a composition containing any of the above substances to an individual, it can stable or improve the individual's sleep quality to achieve the effect of preventing diseases caused by sleep disorders.

Furthermore, in the embodiments of the invention, the composition can be a pharmaceutical composition, a nutritional supplement or a food. For example, when the composition is a pharmaceutical composition, the composition at least includes a pharmaceutically effective amount of *Lactobacillus brevis* ProGA28 or/and its metabolites, and a pharmaceutically acceptable carrier; when the composition is a nutritional supplement, the composition at least includes an effective amount of *Lactobacillus brevis* ProGA28 or/and its metabolites and a carrier which is acceptable for food production.

In addition, the composition can be prepared in various forms according to requirements, such as tablets, liquids, powders, and the like.

In an embodiment of the present invention, the dosage of *Lactobacillus brevis* ProGA28 in humans is at least 1.6 mg/kg.

DETAILED DESCRIPTION OF THE PREFERRED EMBODIMENTS

The 16S rRNA sequence of the novel *Lactobacillus brevis* ProGA28 disclosed by this invention is shown as SEQ ID NO: 1, and through BLAST comparison in NCBI Nucleotide collection (nr/nt) database, it found the novel *Lactobacillus brevis* ProGA28 is a novel strain of *Lactobacillus brevis*. The *Lactobacillus brevis* ProGA28 deposited at the Leibniz Institute DSMZ-German Collection of Microorganisms and Cell Cultures (DSM) on 28$^{th}$ May, 2018 under accession number DSM 33167, and deposited at Taiwan Bioresource Collection and Research Center (BCRC) of Food Industry Research and Development Institute on 27$^{th}$ Jun., 2019 under accession number BCRC 910910.

Figure 1:
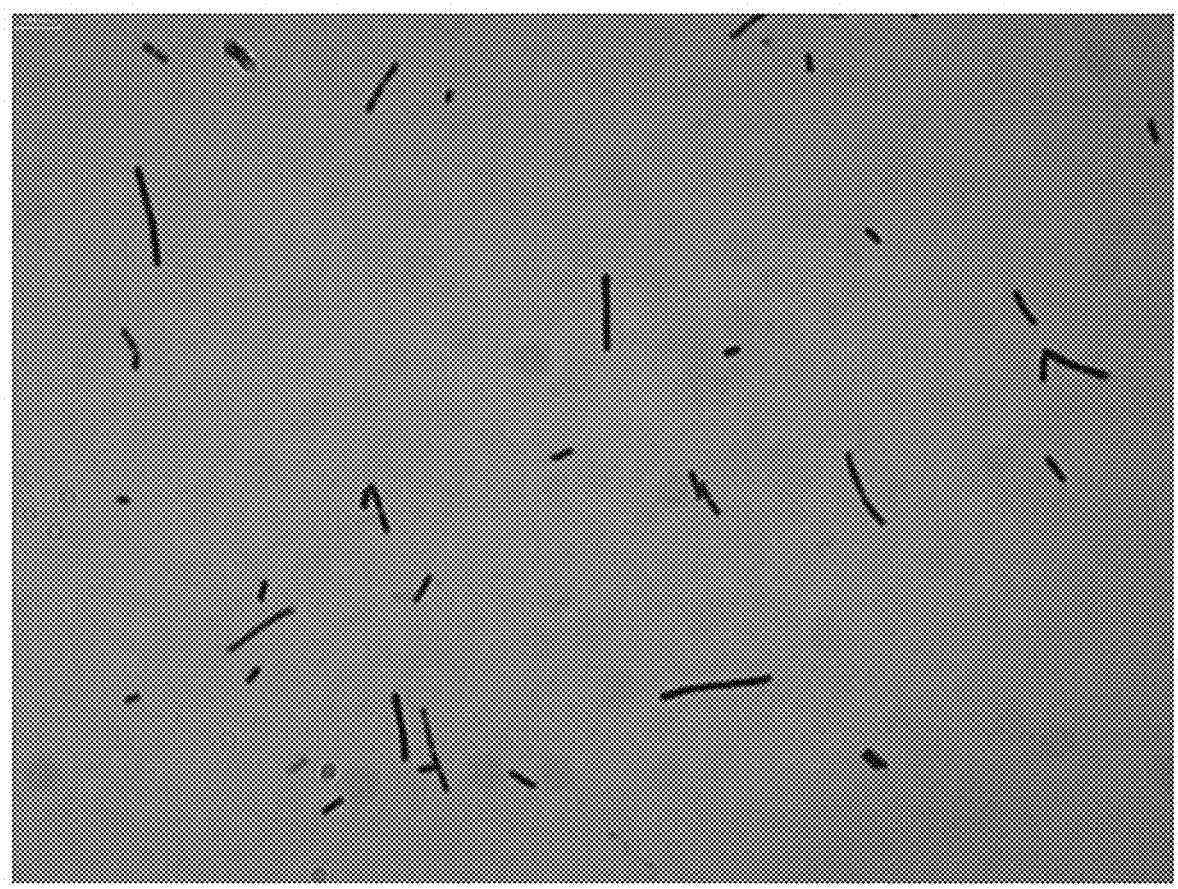
FIG. 1 shows the positive results of the Gram stain of the novel *Lactobacillus brevis* ProGA28 disclosed in the present invention.
Figure 2:
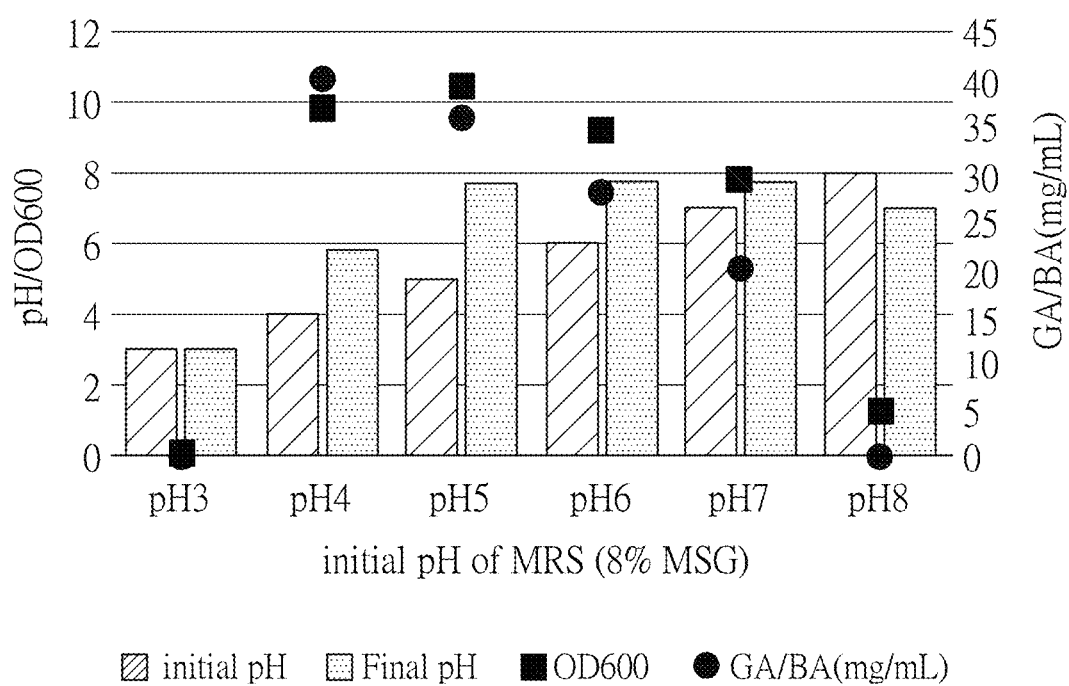
FIG. 2 shows the ability of the novel *Lactobacillus brevis* ProGA28 of the present invention to grow GABA in a media with different pH.

Furthermore, the novel *Lactobacillus brevis* ProGA28 is isolated from natural fermented pickles and can grow on the MRS medium. As shown in FIG. 1, the novel *Lactobacillus brevis* ProGA28 is a gram-positive bacterium, which can be observed under a microscope as a single or tandem of brevibacterium, and can grow at 30° C. or 37° C. under aerobic or anaerobic conditions, preferably 30° C.; as shown in FIG. 2, when using the MRS medium, it can tolerate 8% MSG (monosodium Glutamate) and still have the ability to grow and produce GABA; when using the medium containing 8-12% MSG, 1-3% glucose, 1.5-3% yeast extract and 0.01~0.08% magnesium sulfate, it can be cultured under the pH 4~7, at 30~37° C. for 2~4 days and produce the GABA, which is about 60~110 mg/mL.

The novel *Lactobacillus brevis* ProGA28 metabolites disclosed in the invention means that it is obtained from a medium containing monosodium glutamate which has been cultured the *Lactobacillus brevis* ProGA28 and then removed the bacteria of *Lactobacillus brevis* ProGA28.

Hereinafter, in order to further illustrate the present invention, an embodiment will be described in detail as follows.

The dosage of the test products used in the following examples is based on the daily human consumption of 8.3 mg/kg, and then according to the body surface area model coefficient of 6.2 to calculate the standard feeding dosage for rats being 52 mg/kg which is set as 1.0x dose given in the following examples.

The animals used in the following examples are hypertensive rats (hereinafter referred to as SHR rats), which have the characteristics of having many sleep interruptions and sleep fragmentations, and higher sympathetic nerve activity during sleep than normal rats.

The "sleep stage" called in the following examples includes the following three stages: awake (AW); quiet sleep (QS) which is equivalent to human non-rapid eye movement sleep (NREM) and paradoxical sleep (PS) which is equivalent to human rapid eye movement sleep (REM).

The analysis techniques used in the following examples are described as follows:

Frequency domain analysis of brain waves and myoelectric waves: each 16 seconds (1024 points) of brain wave signal acquisition is called a time window (or epoch), and is compared with 8 seconds before the next time window (50%) overlap for analysis. The fast Fourier transform is used to estimate the power spectral density and evaluate the activity of brain waves in different frequency bands.

Sleep structure analysis and judgment method: using the threshold of mean power frequency (TMPF) of brain wave and the power of myoelectric wave as the criterion for determining sleep state, specifically, when the frequency of brain wave is greater than the threshold of electromyography (TEMG), it is defined as the awake stage; if the frequency of brain wave and the EMG are lower, it is defined as a quiet sleep stage; when the frequency of brain wave is higher and the EMG is lower, it is defined as a paradoxical sleep stage.

Sleep time estimation: upon to different requirements to set different time windows for analysis, and then make manual and fine adjustments by professionals to make the analysis of sleep staging achieve a correct rate of more than 95%. With the definitions of the sleep stages, the relevant parameters including the time of quiet sleep and paradoxical sleep (QS+PS), the number of fall asleep in the estimated time and the average sleep time of single sleep (mins/number) can be obtained for evaluating the stability of animal sleep.

The frequency bands of brain wave are defined as follows: alpha: 10-13 Hz; beta: 13-32 Hz; theta: 6-10 Hz; delta: 0.5-4 Hz. The standardized frequency bands can assess the sleep quality of rats.

EXAMPLE 1

Manufacturing the *Lactobacillus Brevis* ProGA28 Metabolites

Provided a novel *Lactobacillus brevis* ProGA28 disclosed in the present invention and cultured on the MRS medium at 30~37° C. for 8~16 hours. After activation and proliferation procedures, the novel *Lactobacillus brevis* ProGA28 was cultured on the MRS medium containing 8~12% MSG, 1~3% glucose, 1.5~3% yeast extract and 0.01~0.08% magnesium sulfate, in the range of pH4~pH7, at 30~37° C. for 48-72 hours. Until the GABA output was to 110 mg/ml or more, treated with activated carbon, and then removed the bacteria and activated carbon. After concentrated and spray-dried, the obtained product was the probiotic metabolite disclosed in the present invention, and it is found that it contains about 20% gamma-aminobutyric acid.

EXAMPLE 2

Analysis Results of the *Lactobacillus Brevis* ProGA28 Metabolites

Commercially available *Lactobacillus brevis* was taken, and the metabolites of commercially available *Lactobacillus brevis* were prepared by the method disclosed in Example 1. The metabolites of the commercially available *Lactobacillus brevis* and the metabolites of the *Lactobacillus brevis* ProGA28 were analyzed by thin layer chromatography analysis and HPLC analysis, respectively, and the results were shown in FIG. 3 and FIG. 4, wherein, thin layer chromatography analysis was developed with n-BuOH/AcOH/water with a volume ratio of 15/1/1, and then developed with ninhydrin; the conditions of HPLC analysis: C8 column, 5 μm/4.6x250 mm, extracted with 0.1% TFA for 20 minutes, and the analysis wavelength was 214 nm.

Figure 3:
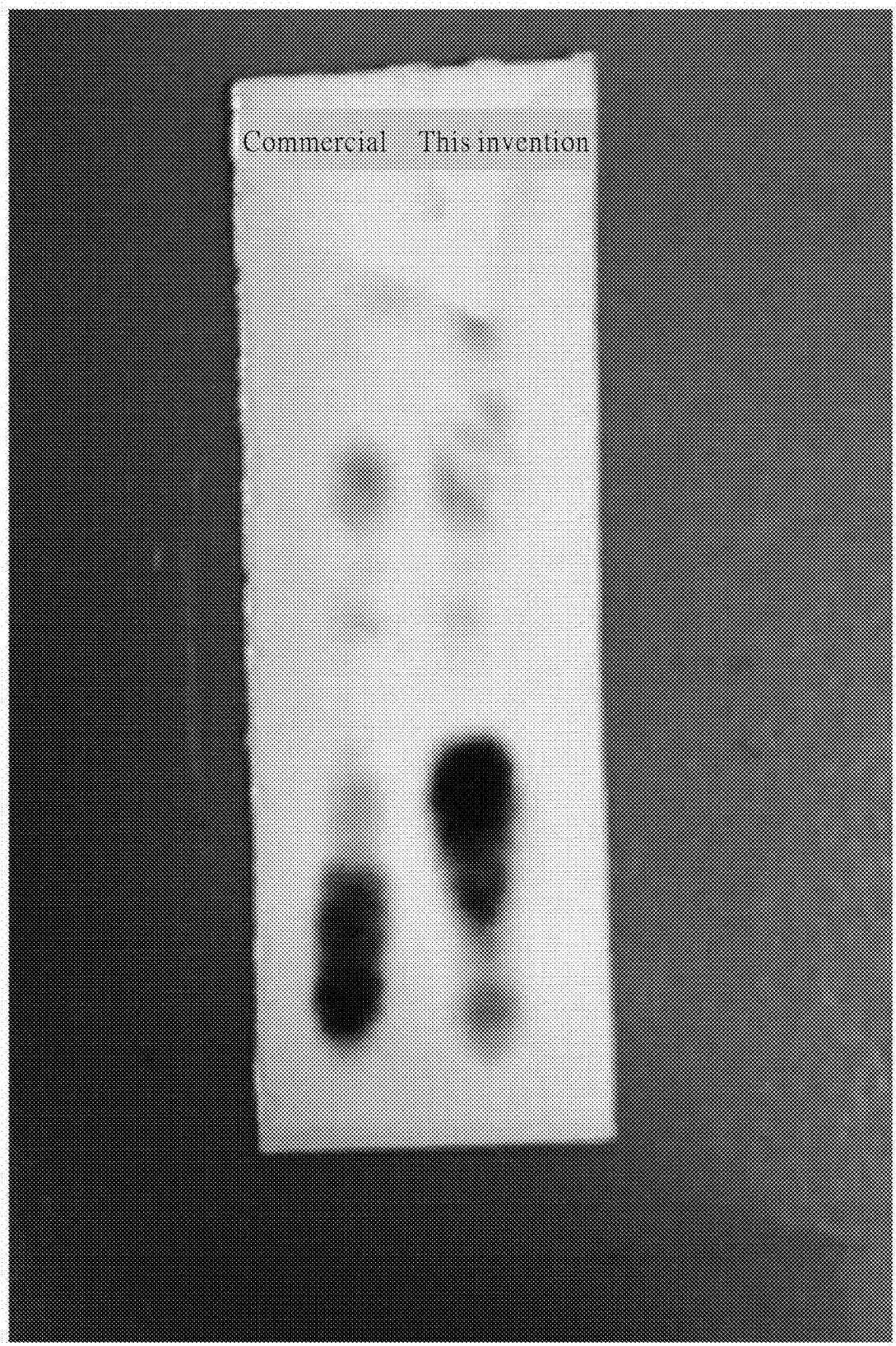
FIG. 3 is the result of thin-layer chromatography analysis of the metabolites of the novel *Lactobacillus brevis* ProGA28 disclosed in the present invention and the metabolites of the commercially available *Lactobacillus brevis*.
Figure 4:
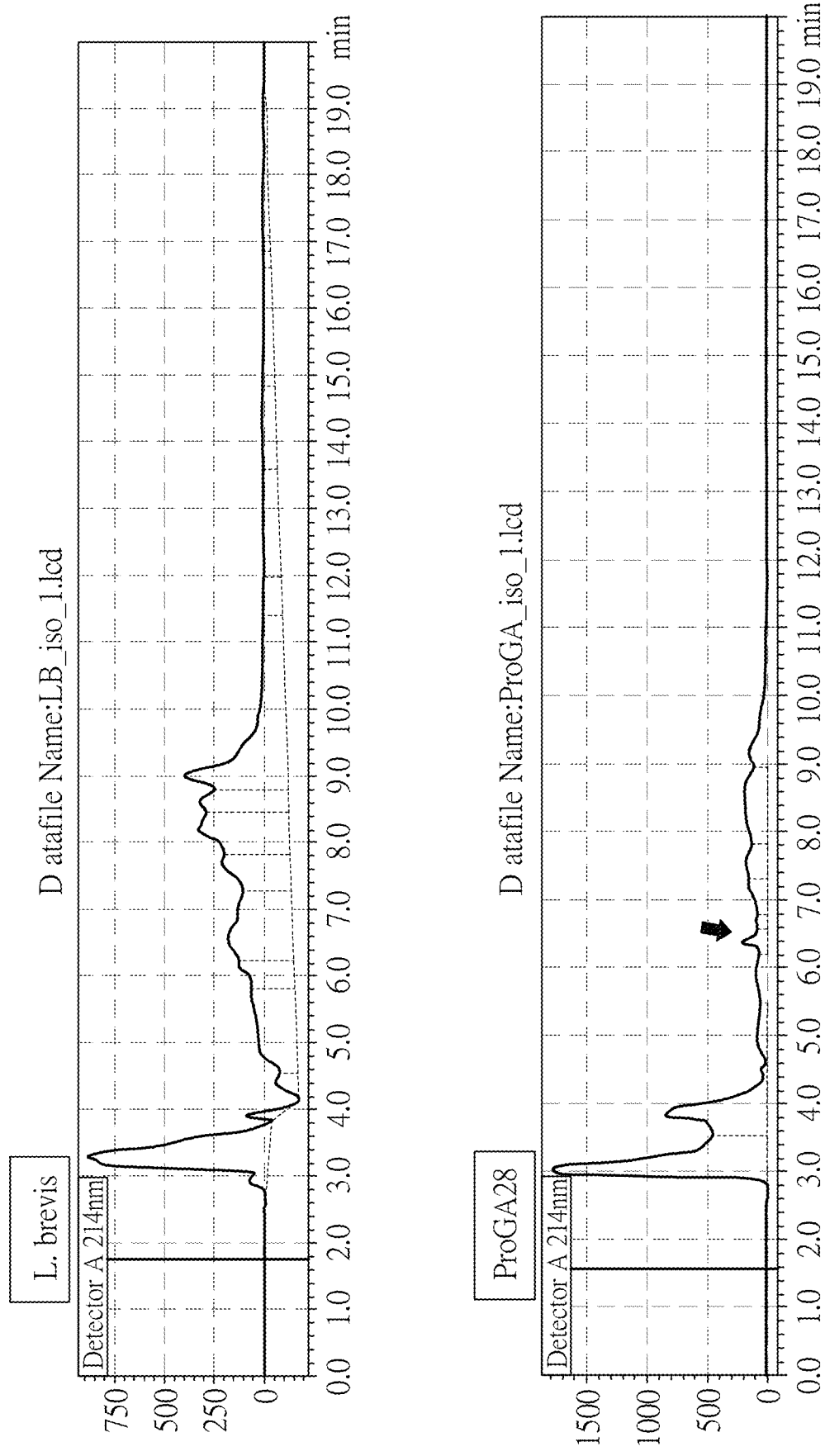
FIG. 4 is the result of HPLC analysis of the metabolites of the novel *Lactobacillus brevis* ProGA28 disclosed in the present invention and the metabolites of the commercially available *Lactobacillus brevis*.

According to the results of FIGS. 3 and 4, it shows that the metabolites of the novel *Lactobacillus brevis* ProGA28 disclosed in the present invention are different from the metabolites of commercially available *Lactobacillus brevis*, and from FIG. 4, it can be clearly understood that the active ingredients in the metabolites of the novel *Lactobacillus brevis* ProGA28 disclosed in the present invention should exist at residence time of 6-7 minutes, which is different from the component of the metabolites of the commercially available *Lactobacillus brevis*.

In other words, although the novel *Lactobacillus brevis* ProGA28 disclosed in the present invention belongs to *Lactobacillus brevis*, it is a novel strain with characteristics different from existing *Lactobacillus brevis* strains, and the ingredients of the metabolites prepared by the novel *Lactobacillus brevis* ProGA28 is also completely different from that prepared by commercially available *Lactobacillus brevis*.

Animal Experiment (1)

Took a plurality of 9-week-old male SHR rats and raise them in a environment with a light-dark cycle of 12:12 hours, a room temperature maintained at 22±2° C., and a humidity of 40-70%; and each SHR rat did the implantation operation of the wireless physiological sensor 10 days before the test for recording the follow-up brain waves, myoelectric waves, ECG, and triaxial acceleration signals.

The SHR rats were randomly divided into groups and administered to A or Treatment Bs, respectively, and the dosages were 0.5× and 1.0×, respectively, wherein:

Treatment A: *Lactobacillus brevis* ProGA28 metabolites prepared by the example 1;

Treatment B: *Lactobacillus brevis* ProGA28 metabolites prepared by the example 1 and 20% Tryptophan.

Each test product was dissolved in drinking water and administered by tube feeding, the administration time was 1 hour before the light, and the physiological information of each group of rats was recorded at the beginning of the light, as a basis for sleep assessment.

In addition, pure gamma-aminobutyric acid was also administered to the SHR rats, and as described above, the physiological information of SHR rats was detected and recorded as a basis for sleep assessment.

EXAMPLE 4

Sleep Quality Assessment Results

The quality and quantity of sleep in the 24 hours after each test product was fed which was used as the range of sleep assessment:

The quantity of sleep: including the total time of sleep and wakefulness, the number of falling asleep and the average time of each sleep stage (duration) etc., and evaluate the quantity of sleep for each sleep stage; and the sleep of the group fed water is defined as 100%, used for comparing with the other groups fed test products to show the difference in each sleep stage.

The quality of sleep: analyzing ratio of the frequency bands of brain waves from fast to slow (beta: 13-32 Hz; alpha: 10-13 Hz; theta: 6-10 Hz; delta: 0.5-4 Hz) in the quiet sleep, and the analysis results were used as an indicator of sleep quality. The higher proportion of slow waves are in sleep, the quality of sleep is better.

Figure 5:
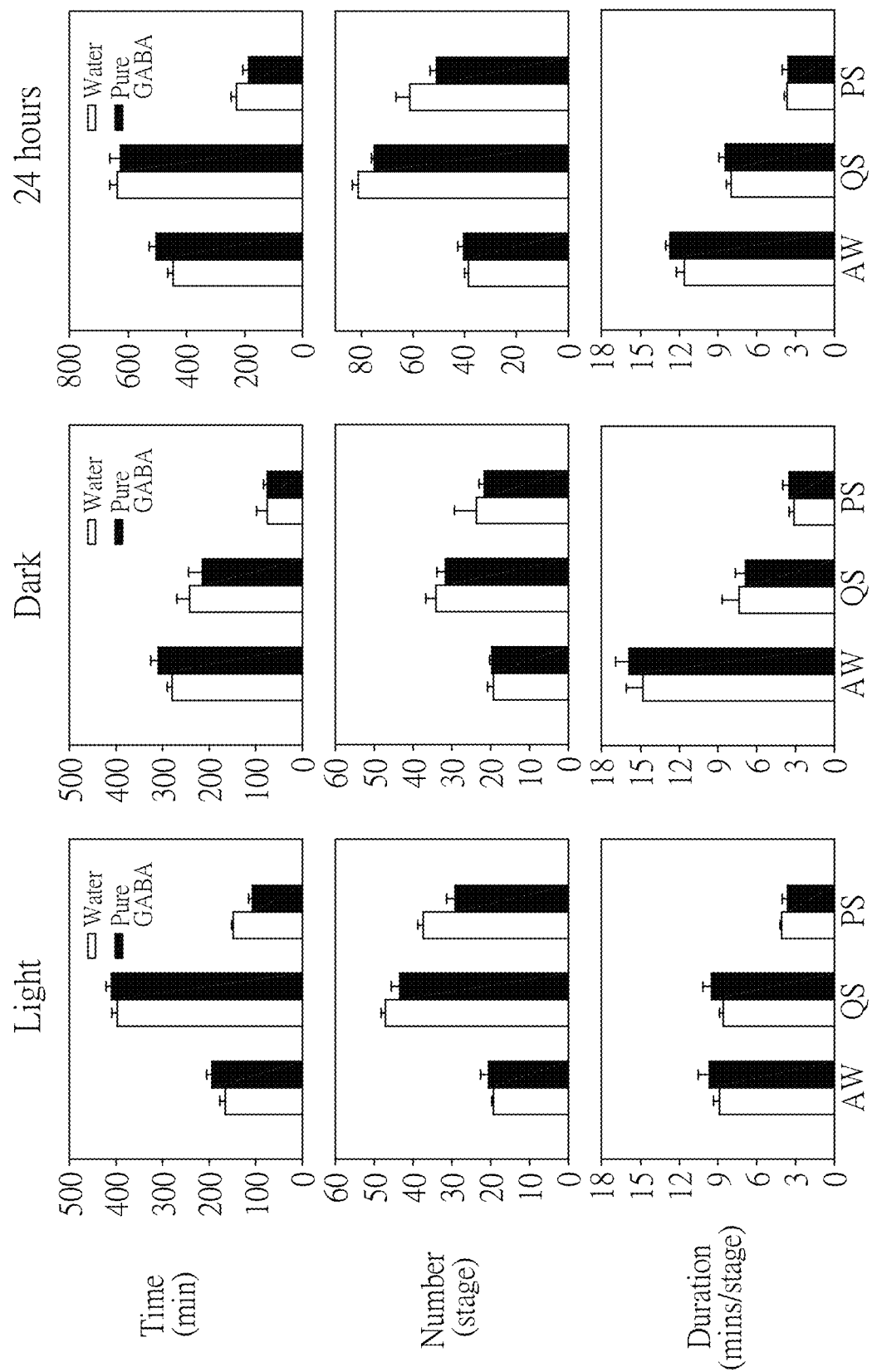
FIG. 5 shows the results of the total time, number of fall asleep and average sleep time of a single stage in three sleep stages after administration of pure γ-aminobutyric acid.
Figure 6:
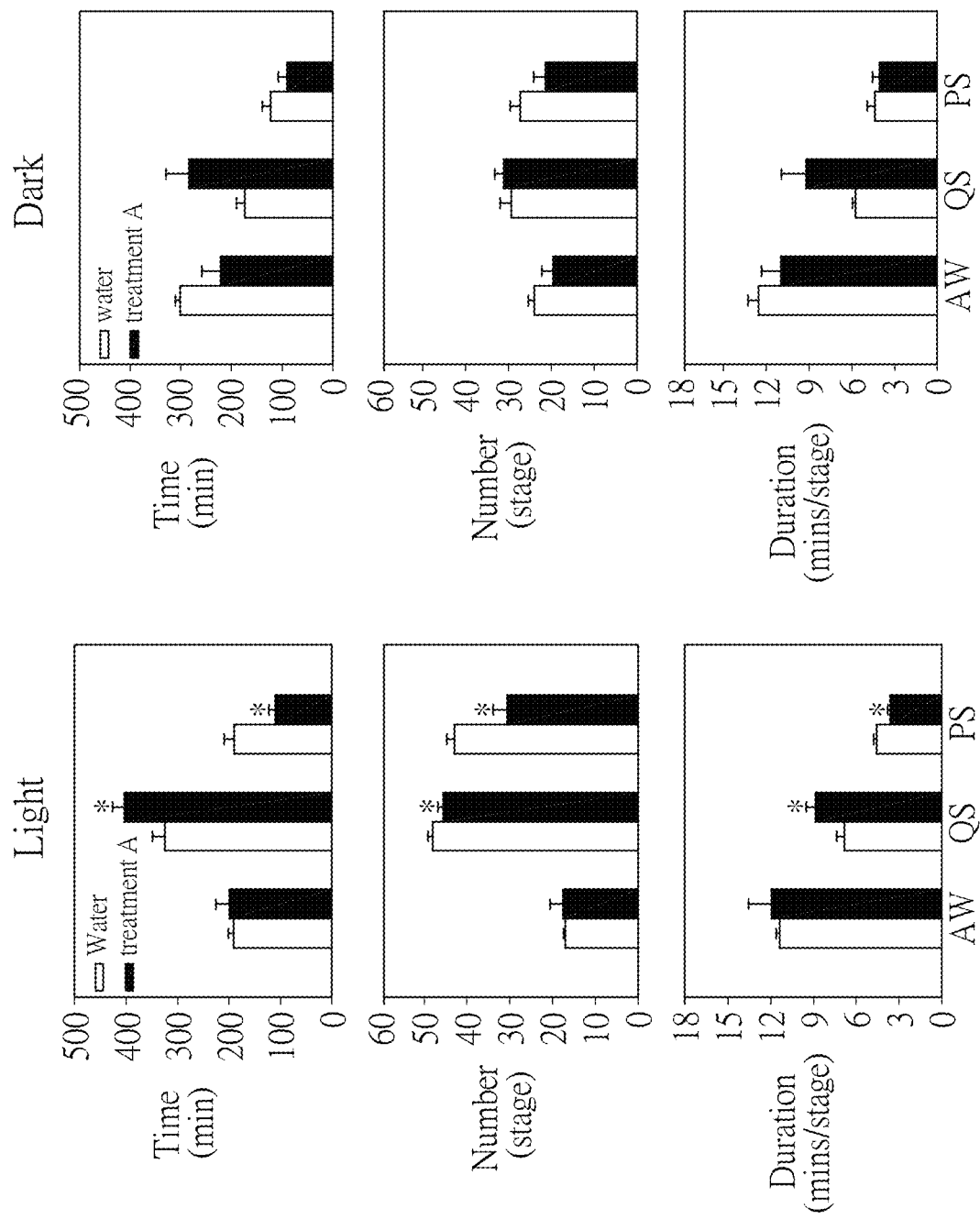
FIG. 6 shows the results of the total time, number of fall asleep and average sleep time of a single phase in the three sleep phases after feeding the 0.5x dose of Treatment A.
Figure 7:
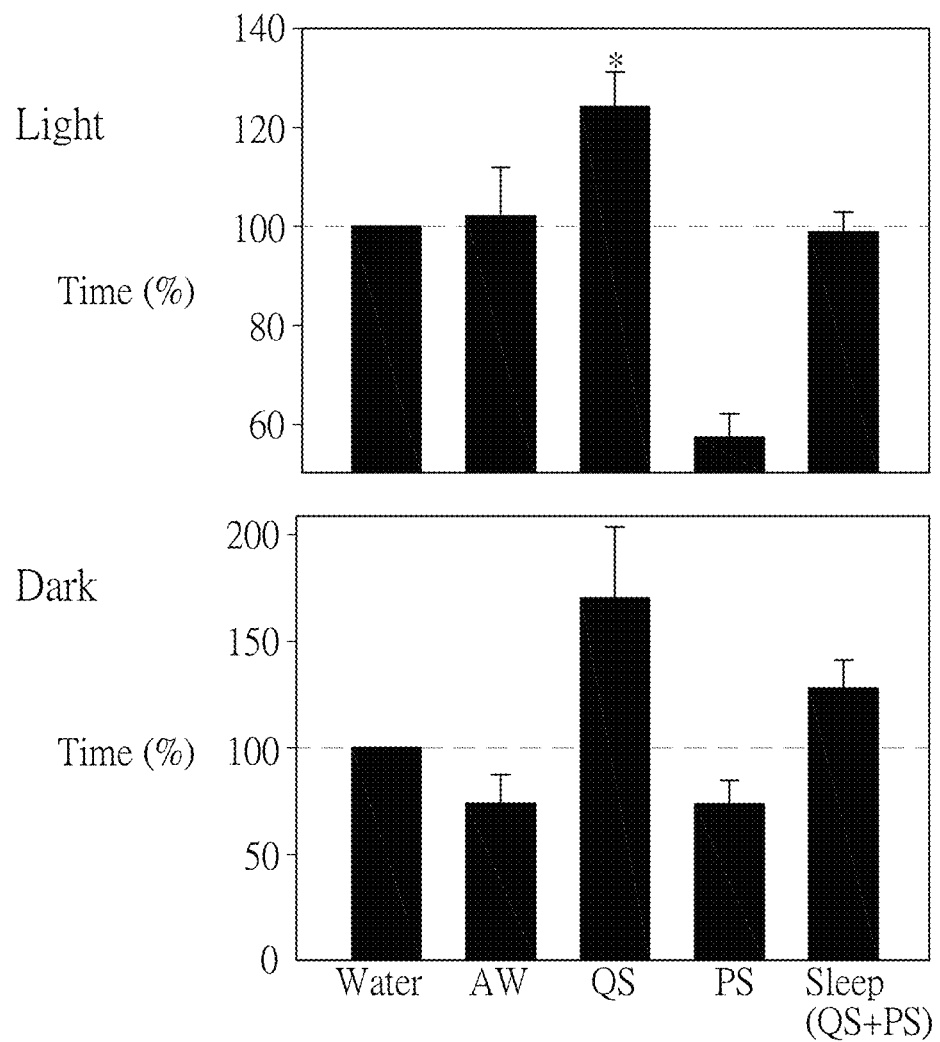
FIG. 7 shows the results of the changing percentage (%) for the three sleep stages and total sleep (QS+PS) by after feeding 0.5x dose of Treatment A, wherein the sleep after feeding water is as the 100% standardized evaluation unit.
Figure 8:
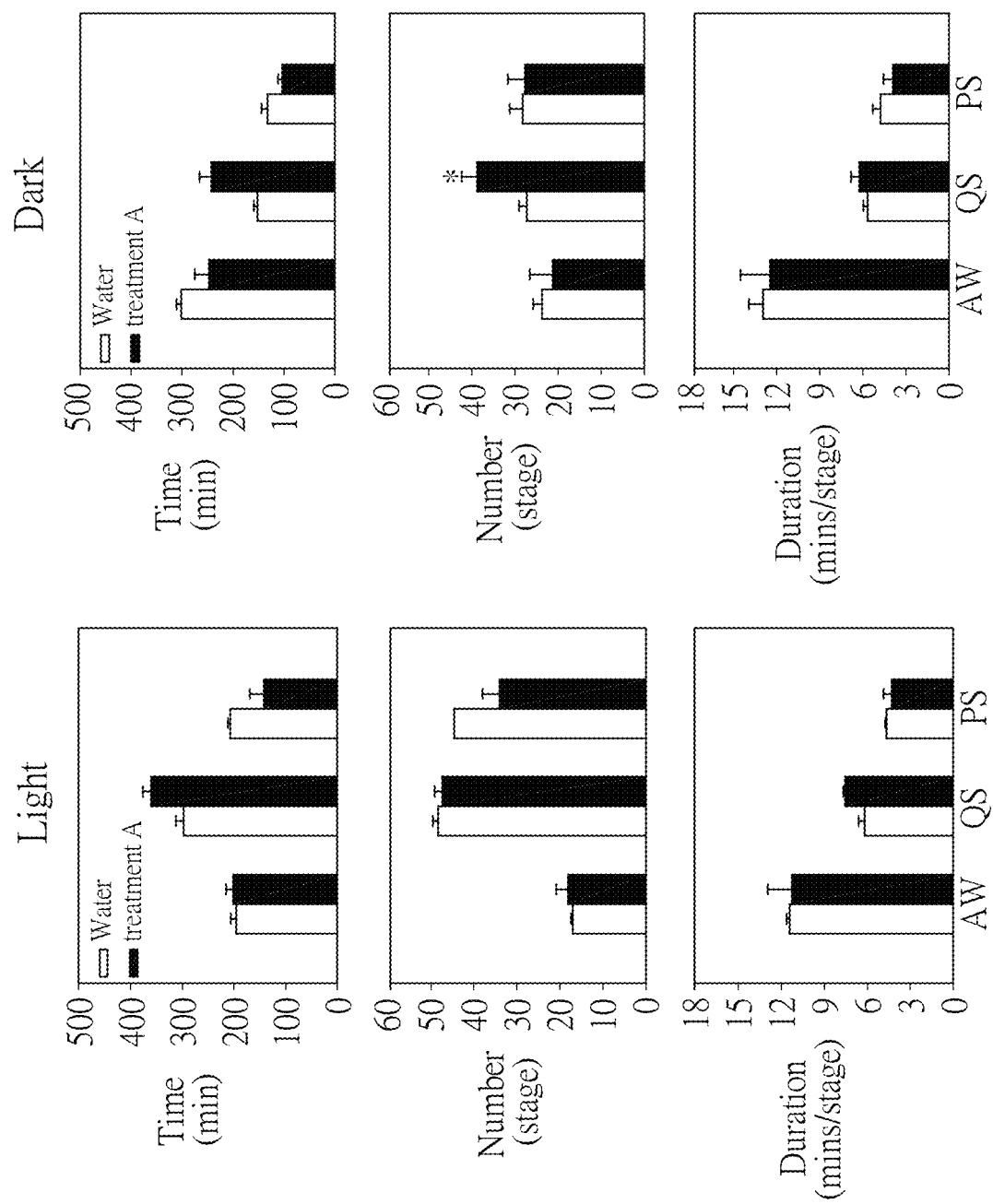
FIG. 8 shows the results of the total time, number of fall asleep and average sleep time of a single phase in the three sleep phases after feeding the 1.0x dose of Treatment A.
Figure 9:
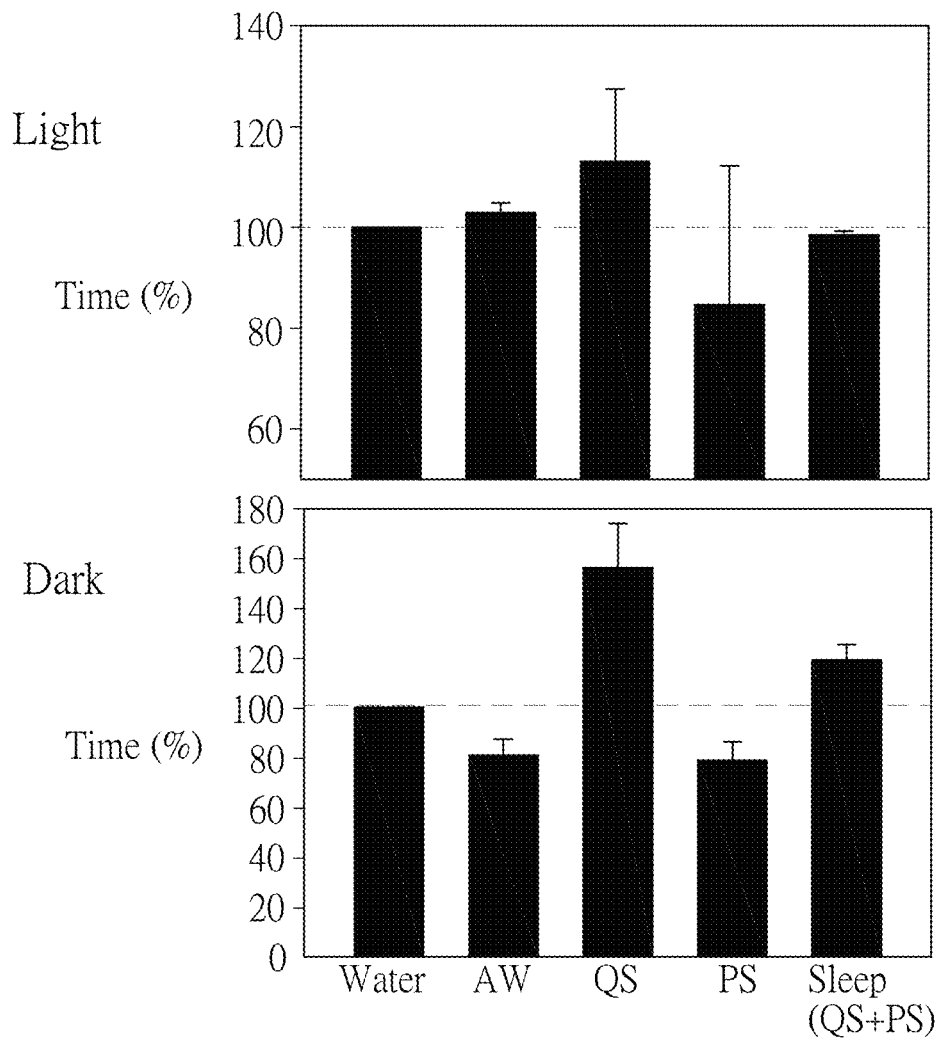
FIG. 9 shows the results of the changing percentage (%) for the three sleep stages and total sleep (QS+PS) by after feeding 1.0x dose of Treatment A, wherein the sleep after feeding water is as the 100% standardized evaluation unit.
Figure 10:
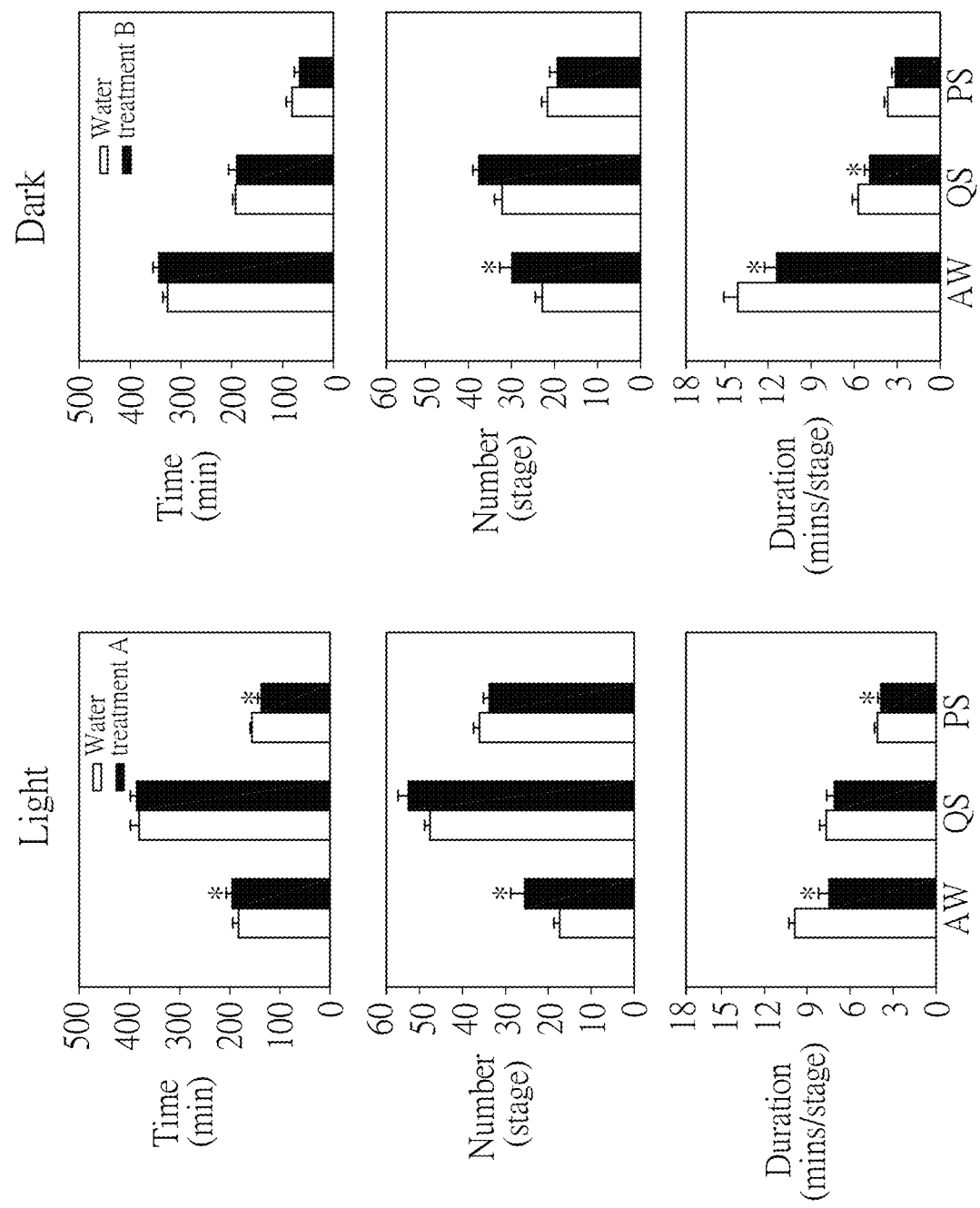
FIG. 10 shows the results of the total time, number of fall asleep and average sleep time of a single phase in the three sleep phases after feeding the 1.0x dose of Treatment B.
Figure 11:
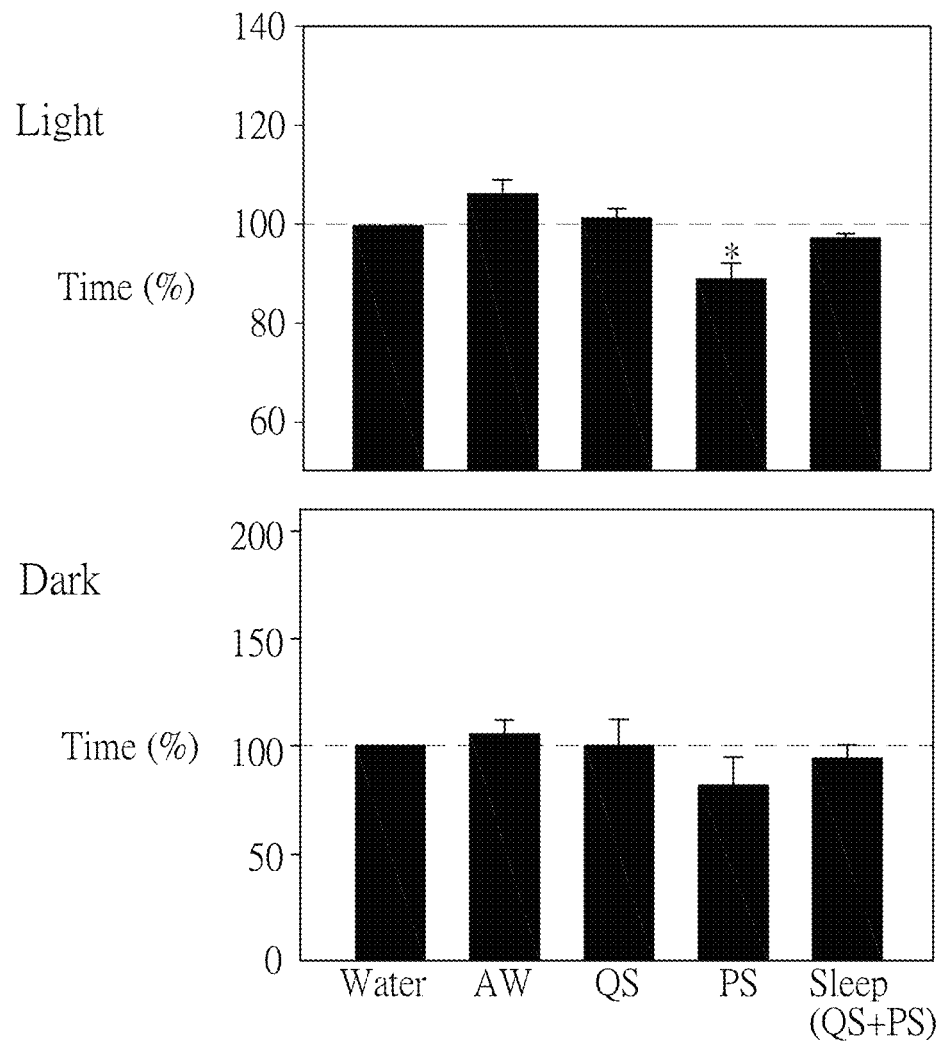
FIG. 11 shows the results of the changing percentage (%) for the three sleep stages and total sleep (QS+PS) by after feeding 0.5x dose of Treatment B, wherein the sleep after feeding water is as the 100% standardized evaluation unit.
Figure 12:
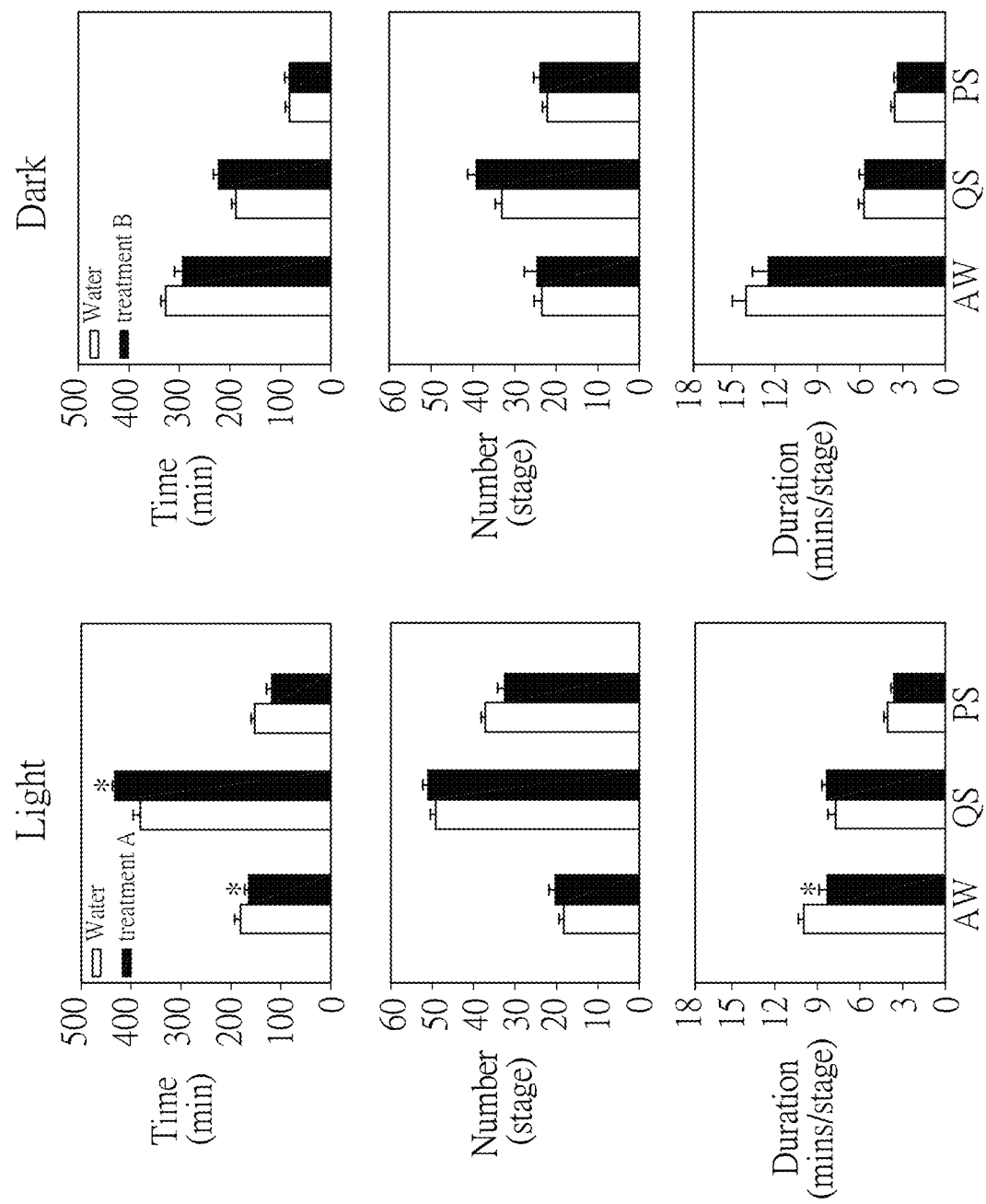
FIG. 12 shows the results of the total time, number of fall asleep and average sleep time of a single phase in the three sleep phases after feeding the 1.0x dose of Treatment B.
Figure 13:
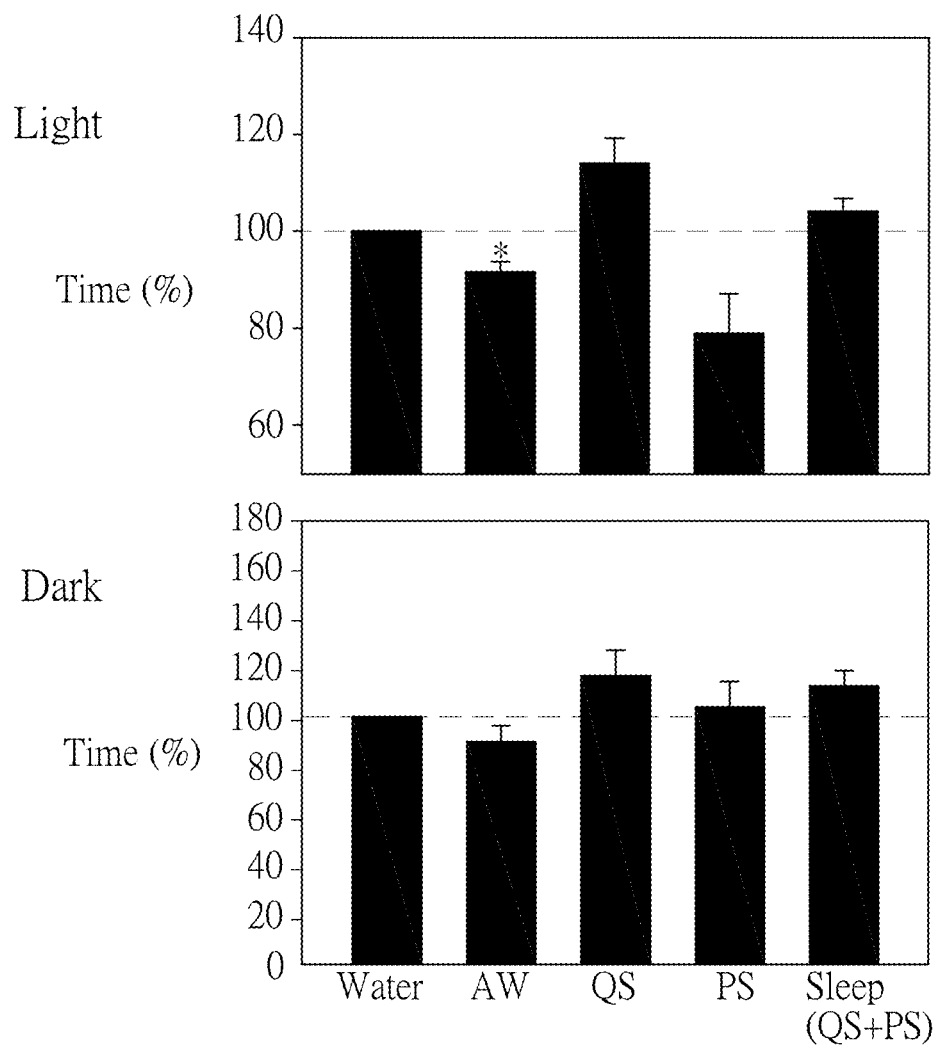
FIG. 13 shows the results of the changing percentage (%) for the three sleep stages and total sleep (QS+PS) by after feeding 1.0x dose of Treatment B, wherein the sleep after feeding water is as the 100% standardized evaluation unit.

Please referred to FIG. 5, which showed that the administration of pure γ-aminobutyric acid was not helpful to increase the sleep quality of rats, and can not increase sleep time; according to the results in FIG. 6 to FIG. 13 and Table 1: when the 0.5× dose of Treatment A was administered, it showed the effect of promoting SHR rats to enter the quiet sleep stage, reducing the time of the paradoxical sleep, increasing the total sleep time, reducing the number of falling asleep and extending the single falling asleep time, and there are also significantly increase the ratio of slow frequency bands of brain waves. Although the administration of Treatment B at a dose of 1.0× slightly increased the time of quiet sleep, it has no effect on sleep stability and autonomic nervous activity.

Comparing the results of FIGS. 3 to 13, it showed that the administration of pure GABA alone was not helpful for the improvement of the quality and quantity of sleep, but the administration of the probiotic metabolites disclosed in the present invention (Treatment A) can improve the quality and quantity of sleep, and can also promote sleep well.

TABLE 1

| Comprehensive test results of sleeping effect | | | | |
|---|---|---|---|---|
| Test product | Sleep time | Sleep stability | Slow frequency bands of brain waves | Sleeping effect |
| A | improve | improve | improve | improve |
| B | not significant | not significant | not significant | not significant |

Animal Experiment (2)

Figure 14:
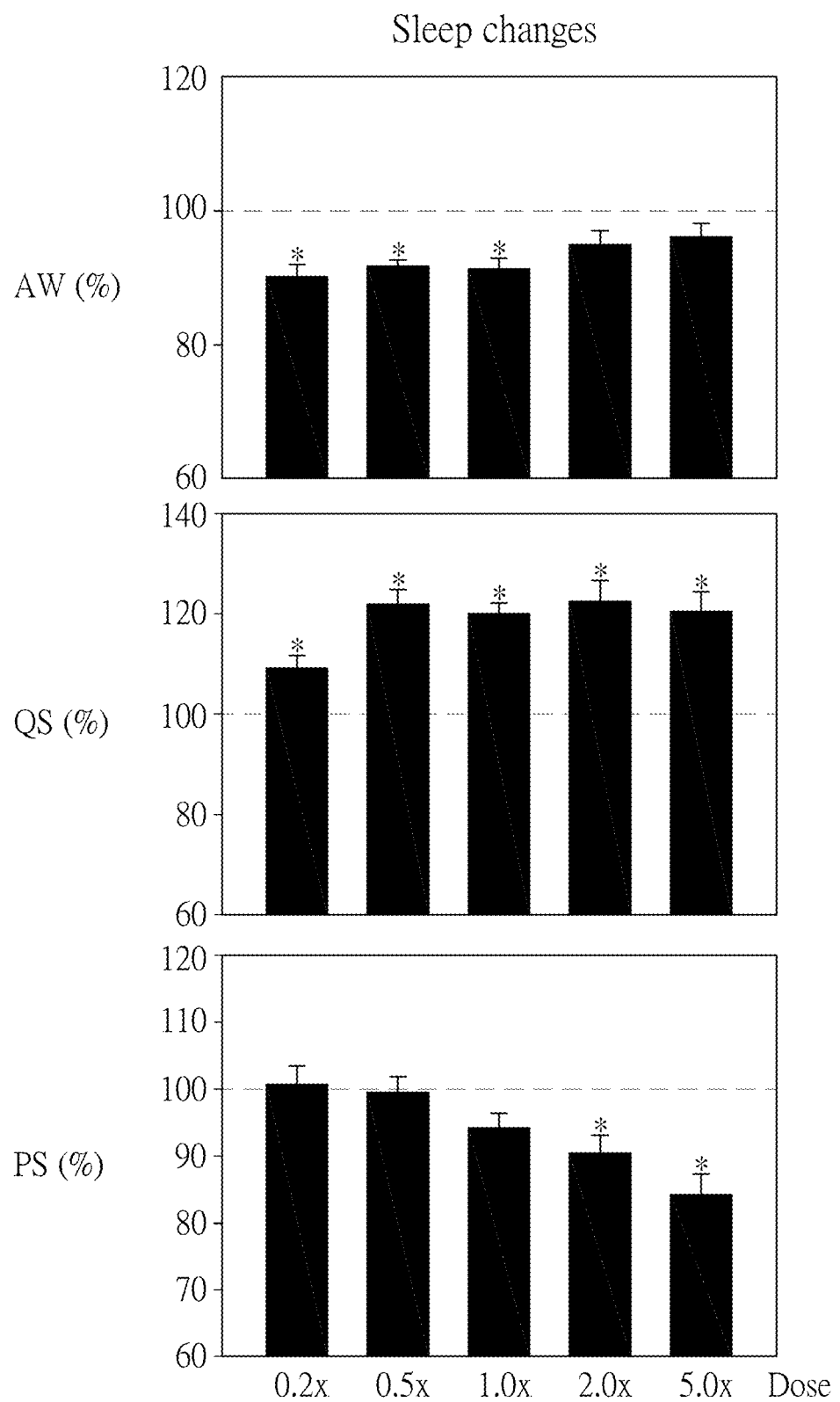
FIG. 14 shows the results of comparing the changes of each sleep stage after administering different doses of Treatment A to rats.

This example detected the sleeping effect of Treatment A (ie the metabolite of *Lactobacillus brevis* ProGA28 disclosed in the present invention) at different doses: 0.2x, 0.5x, 1.0x, 2.0x and 5.0x. The results are shown in FIG. 14 to FIG. 16, and Table 2.

From the results in Table 2, it showed that administering the metabolite of *Lactobacillus brevis* ProGA28 disclosed in the present invention at the lowest dose (0.2×) can reduce the rat's wake time and improve the total sleep time, and the quality and quantity of sleep. The data showed that the preferred dosage of the metabolite of *Lactobacillus brevis* ProGA28 disclosed in the present invention is 0.2×~1.0×.

Furthermore, another group of rats was used to observe the effect for sleep of changing the feeding time. In the group, the feeding time of Treatment A in dose of 0.5× was 12 hours earlier (12 hours before the sleep recording) and then detected the quality and quantity of sleep and the changes of brain waves of the rats in this group. The results were shown in FIGS. 15-16.

Figure 15:
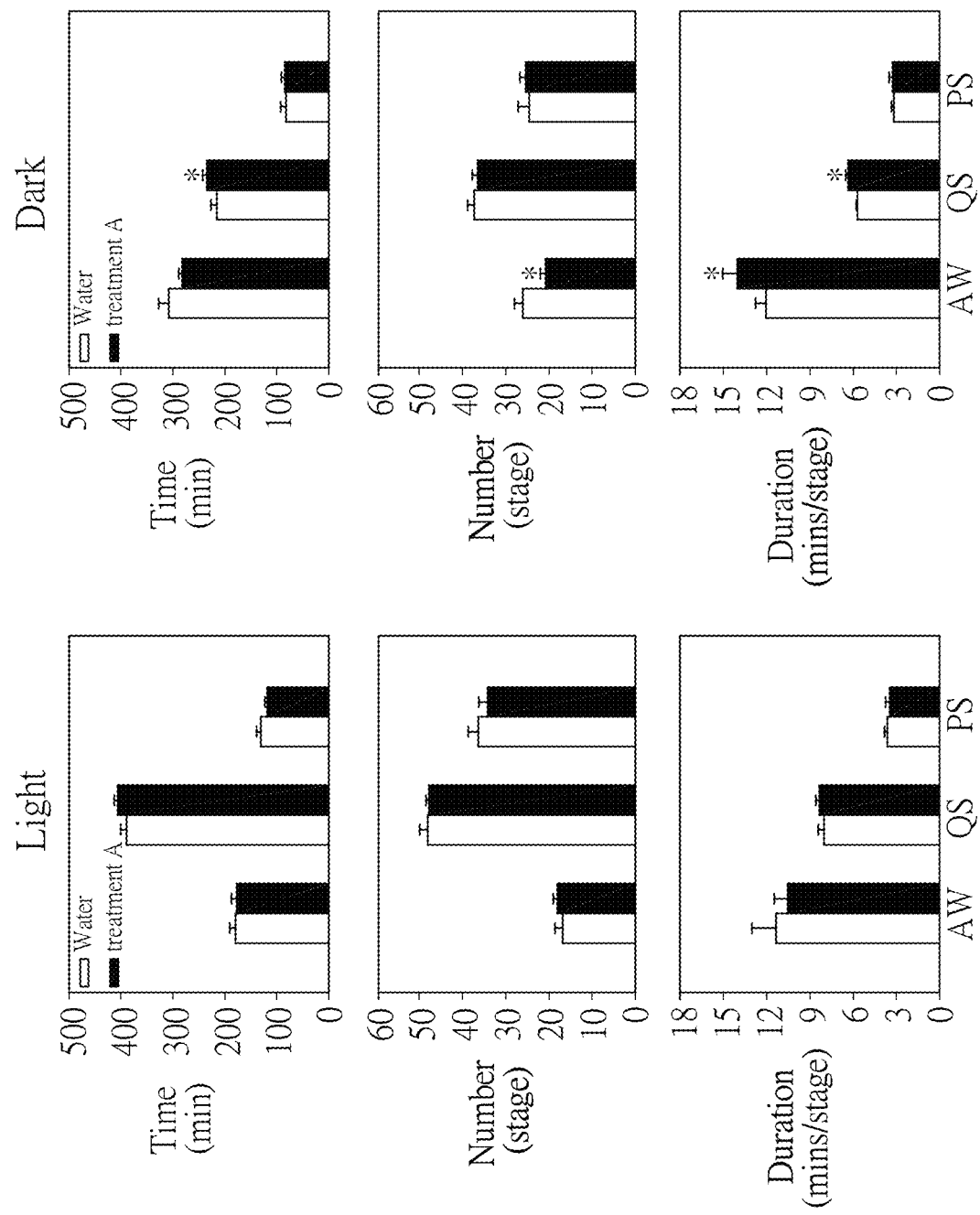
FIG. 15 compares the changes in the total time, number of fall asleep and average sleep time in a single stage of the three sleep stages after feeding of the 0.5x dose of Treatment A 12 hours before recording.
Figure 16:
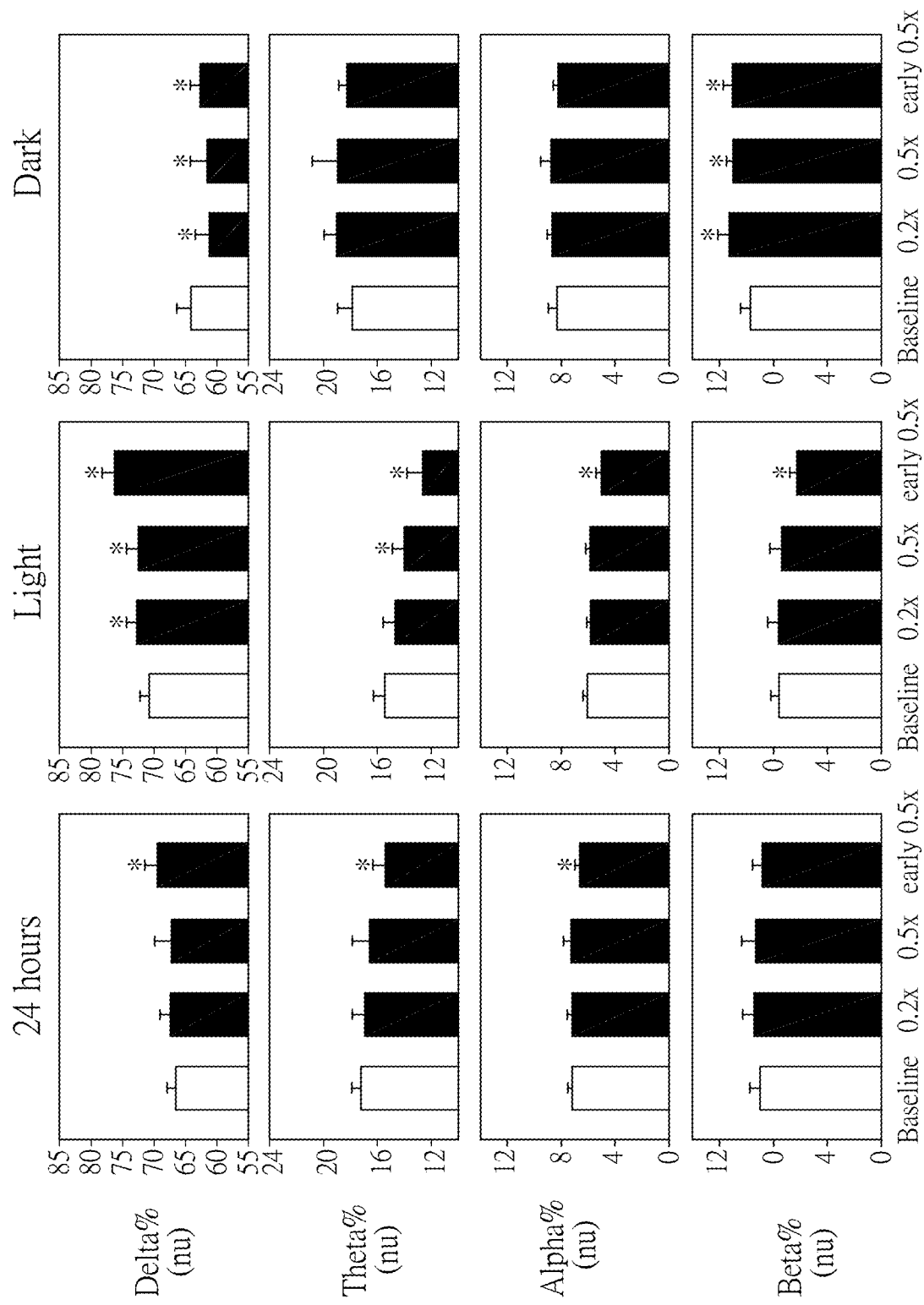
FIG. 16 shows the results of the changing of brain waves in the groups of feeding different doses of Treatment A 12 hours before recording and the control group of feeding water. The results include the ratio of four frequency bands of brain waves (beta:13-32 Hz; alpha: 10-13 Hz; theta: 6-10 Hz; delta: 0.5-4 Hz) in 24 hours, bright period, and dark period during quiet sleep, wherein the value is presented in the form of mean±standard error.

According to the results of FIGS. 15 and 16, it showed that changing the feeding time did not affect the sleep stage of rats, but from the changes of brain waves, it showed that the early administration time can effectively increase the ratio of slow waves in sleep (Delta:0.5-4 Hz).

The effect of different doses on sleep quality and quantity

| Dose of Treatment A | Sleep time | Sleep stability | Slow frequency bands of brain waves | Sleeping effect |
| --- | --- | --- | --- | --- |
| 0.2× | improve | improve | improve | improve |
| 0.5× | improve | improve | improve | improve |
| 1.0× | improve | improve | improve | improve |
| 2.0× | improve | improve | improve | improve |
| 5.0× | improve | improve | improve | improve |

EXAMPLE 6

Separation and Purification of Metabolites of the Novel *Lactobacillus Brevis* ProGA28 and Used for Animal Experiment Took the novel *Lactobacillus brevis* ProGA28 metabolites prepared according to the method of Example 1, mixed it with a strong acid cation exchange resin 1:1 (v/v) and stood for about 30 minutes, and then filtered with the filter paper, collected the filtrate and freeze-dried it into a powder, and the obtained powder was tester A (removal of GABA); mixed the strong acid cation exchange resin adsorbing *Lactobacillus brevis* ProGA28 metabolites with an equal volume of water 1:1 (v/v) and stood for about 30 minutes, then filtered with the filter paper, repeated water washing one time, and then mix with an equal volume of CaCl2 and stood for about 30 minutes, filtered with filter paper, collected the filtrate and freeze-dried into a powder, and the obtained power was tester B (the main component is GABA).

Figure 17A:
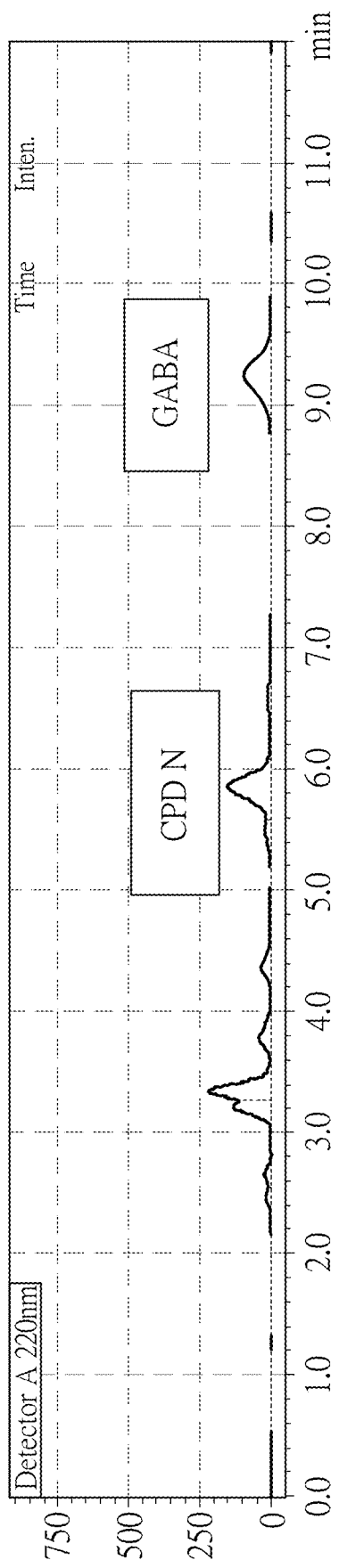
FIG. 17A is the result of HPLC analysis of tester A.
Figure 17B:
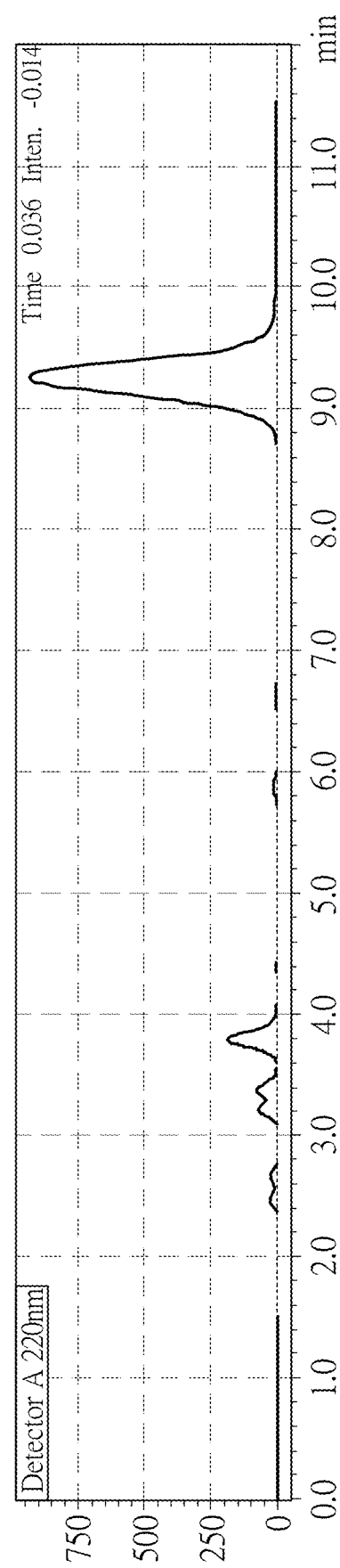
FIG. 17B is the result of HPLC analysis of tester B.
Figure 18A:
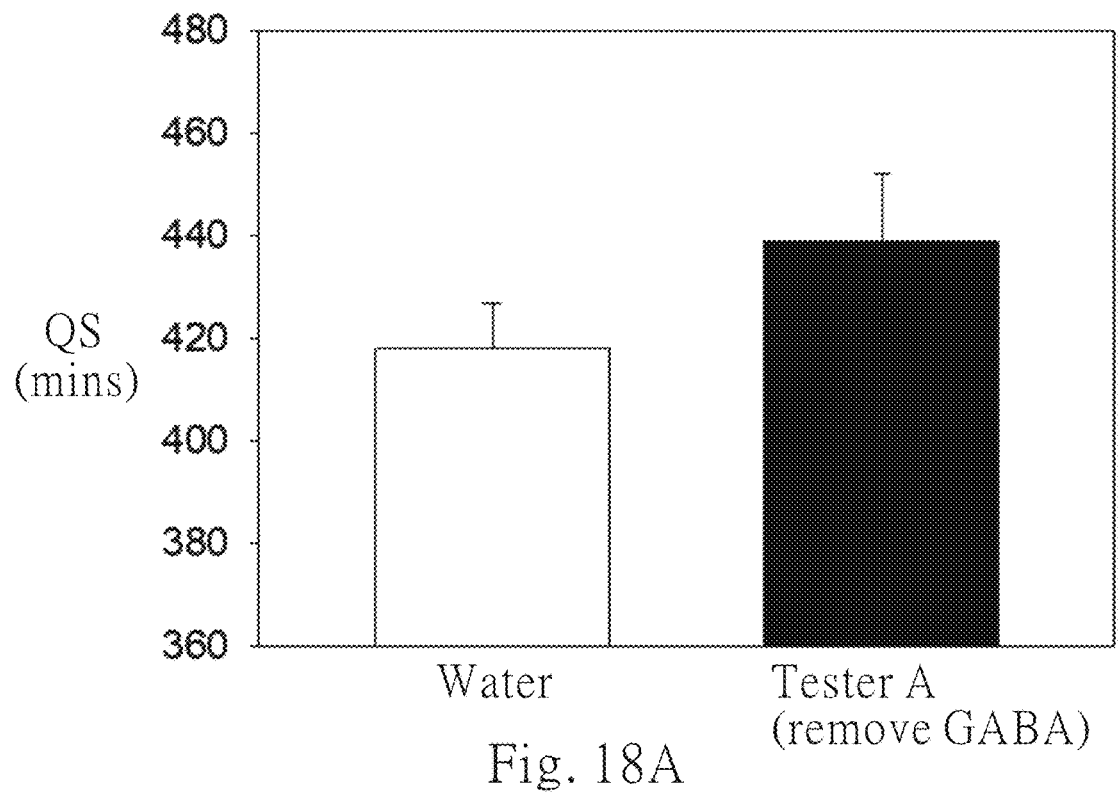
FIG. 18A shows the quiet sleep time of the animal experiment by tester A.
Figure 18B:
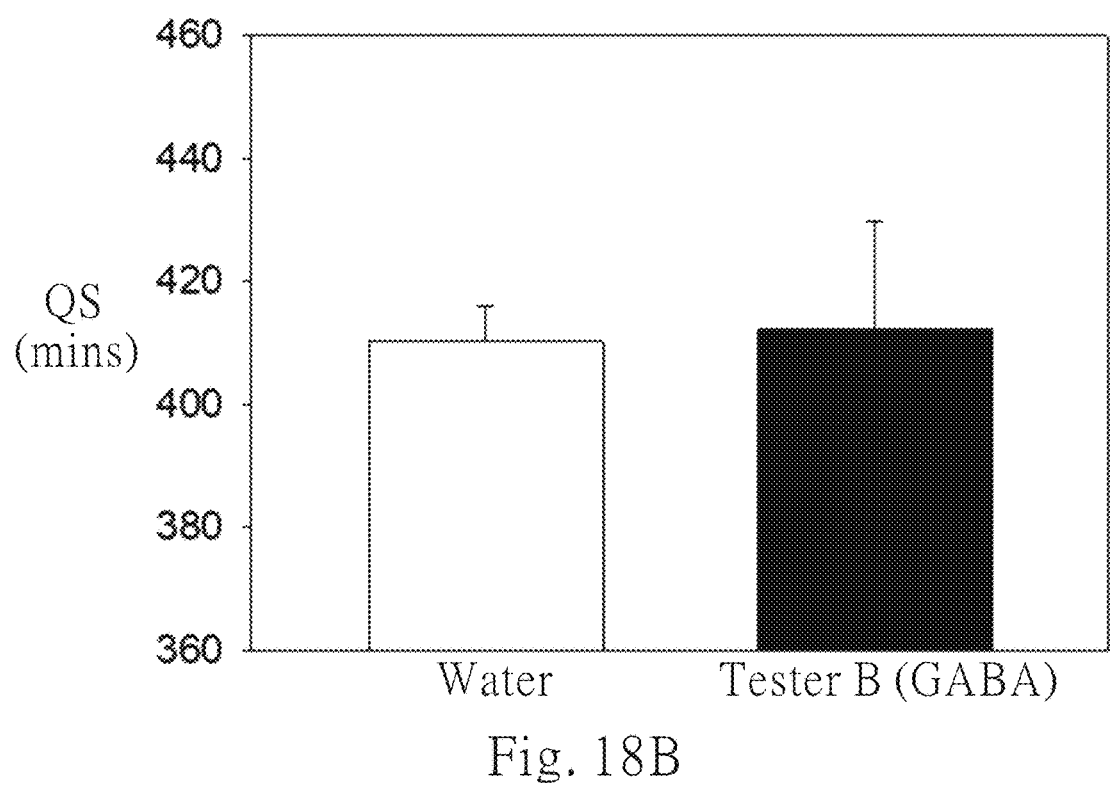
FIG. 18B shows the quiet sleep time of the animal experiment by tester B.

The tester A and the tester B obtained by the above steps were analyzed by HPLC. The analysis conditions referred to Example 2. The result was shown in FIG. 17; according to FIG. 17, it clearly showed that the tester A contained almost no GABA component, but contained CPD N (compound N), and the residence time of CPD N was at about 5-7 minute, and the tester B had a high amount of GABA.

Furthermore, took the tester A and the tester B for animal experiments, respectively, and the experimental procedures referred to Examples 3 and 4. It is found that the tester A had the effect of promoting the quiet sleep, but the tester B did not promote the effect of the quiet sleep. The results showed that the metabolites obtained by culturing of *Lactobacillus brevis* ProGA28 of the present invention can indeed promote the quiet sleep, and the effective ingredient for improving and treating the sleep disorders or promoting the quiet sleep is CPD N, not GABA.

From the results of the above examples, it showed that the metabolites of *Lactobacillus brevis* ProGA28 disclosed in the present invention have the ability to improve sleep quality and promote sleep, and it must be emphasized that the so-called "improved sleep quality" means the metabolites of *Lactobacillus brevis* ProGA28 disclosed in the present invention can not only prolong the sleep time of an individual, but also increase the ration of slow waves in the brain to achieve the effect of improving the quality and quantity of sleep. Therefore, the *Lactobacillus brevis* ProGA28 and its metabolites disclosed in the present invention are used as the effective ingredient of the composition for improving or treating sleep disorders or related diseases, and the composition can be prepared as a pharmaceutical composition, nutrition supplements or foods according to requirements, and the dosage contained therein is preferably a low dosage, for example, for a 60 kg adult, the dosage is about at least 1.6 mg/kg.

[Biological Material Deposit]

Taiwan Bioresource Collection and Research Center (BCRC) of Food Industry Research and Development Institute on 27 Jun., 2019 under accession number BCRC 910910.

Leibniz Institute DSMZ-German Collection for of Microorganisms and Cell Cultures (DSM) on 28th May, 2019 under accession number DSM 33167,

What is claimed is:

1. A method for treating or improving sleep disorders, comprising administering a therapeutically effective amount of metabolites of an isolated strain of *Lactobacillus brevis* ProGA28 to a patient in need thereof, wherein the strain of *Lactobacillus brevis* ProGA28 is deposited at the Leibniz-Institute DSMZ - German Collection of Microorganisms and Cell Cultures (DSM) under the Budapest Treaty, having accession number DSM 33167, wherein the metabolites of the strain of *Lactobacillus brevis* ProGA28 are obtained from a medium with monosodium glutamate (MSG), from which the strain is removed after it has been cultured.

2. The method of claim 1, wherein the therapeutically effective amount of the metabolites of the strain of *Lactobacillus brevis* ProGA28 is at least 1.6 mg/kg.

3. The method of claim 1, wherein the strain's 16S rRNA sequence is SEQ ID NO: 1.

4. The method of claim 3, wherein the therapeutically effective amount of the metabolites of the strain is at least 1.6 mg/kg.

5. The method of claim 1, wherein the strain of *Lactobacillus brevis* ProGA28 is isolated from a fermented pickle.

6. The method of claim 5, wherein the therapeutically effective amount of the metabolites of the strain is at least 1.6 mg/kg.

* * * * *